United States Patent [19]

McIntyre

[11] Patent Number: 4,646,510
[45] Date of Patent: Mar. 3, 1987

[54] METHOD OF AND APPARATUS FOR MAKING POWDER-FILLED POUCHES AND THE LIKE

[75] Inventor: Frederic S. McIntyre, Wellesley, Mass.

[73] Assignee: Acumeter Laboratories, Inc., Marlborough, Mass.

[21] Appl. No.: 824,876

[22] Filed: Jan. 31, 1986

[51] Int. Cl.⁴ .................... B65B 9/02; B65B 11/58
[52] U.S. Cl. .................................... 53/449; 53/451; 53/141; 53/554
[58] Field of Search ............... 53/410, 449, 450, 451, 53/128, 141, 383, 553, 554, 170

[56] References Cited

U.S. PATENT DOCUMENTS

| | | | |
|---|---|---|---|
| 2,525,651 | 10/1950 | Clunan | 53/141 X |
| 2,903,833 | 9/1959 | Jones | 53/141 X |
| 3,014,233 | 12/1961 | Gibbons | 53/553 X |
| 3,456,564 | 7/1969 | McCandless | 53/141 X |
| 3,595,204 | 1/1970 | McIntyre | 118/8 |
| 3,641,737 | 2/1972 | Tamagni | 53/554 |
| 4,004,399 | 1/1977 | Borrello | 53/554 |
| 4,085,560 | 4/1978 | McClosky | 53/449 |
| 4,437,294 | 3/1984 | Romagnoli | 53/553 |

Primary Examiner—Horace M. Culver
Attorney, Agent, or Firm—Rines and Rines Shapiro and Shapiro

[57] ABSTRACT

A method of and apparatus for helical screw controlled-quantity extrusion of powdered material, such as, for example, moisture-absorbent super fine powders, with automatic filling of hot-melt laminated pouches, at least partially porous, as for use in diaper or other similar applications, and while obviating hazardous release of the powder.

14 Claims, 1 Drawing Figure

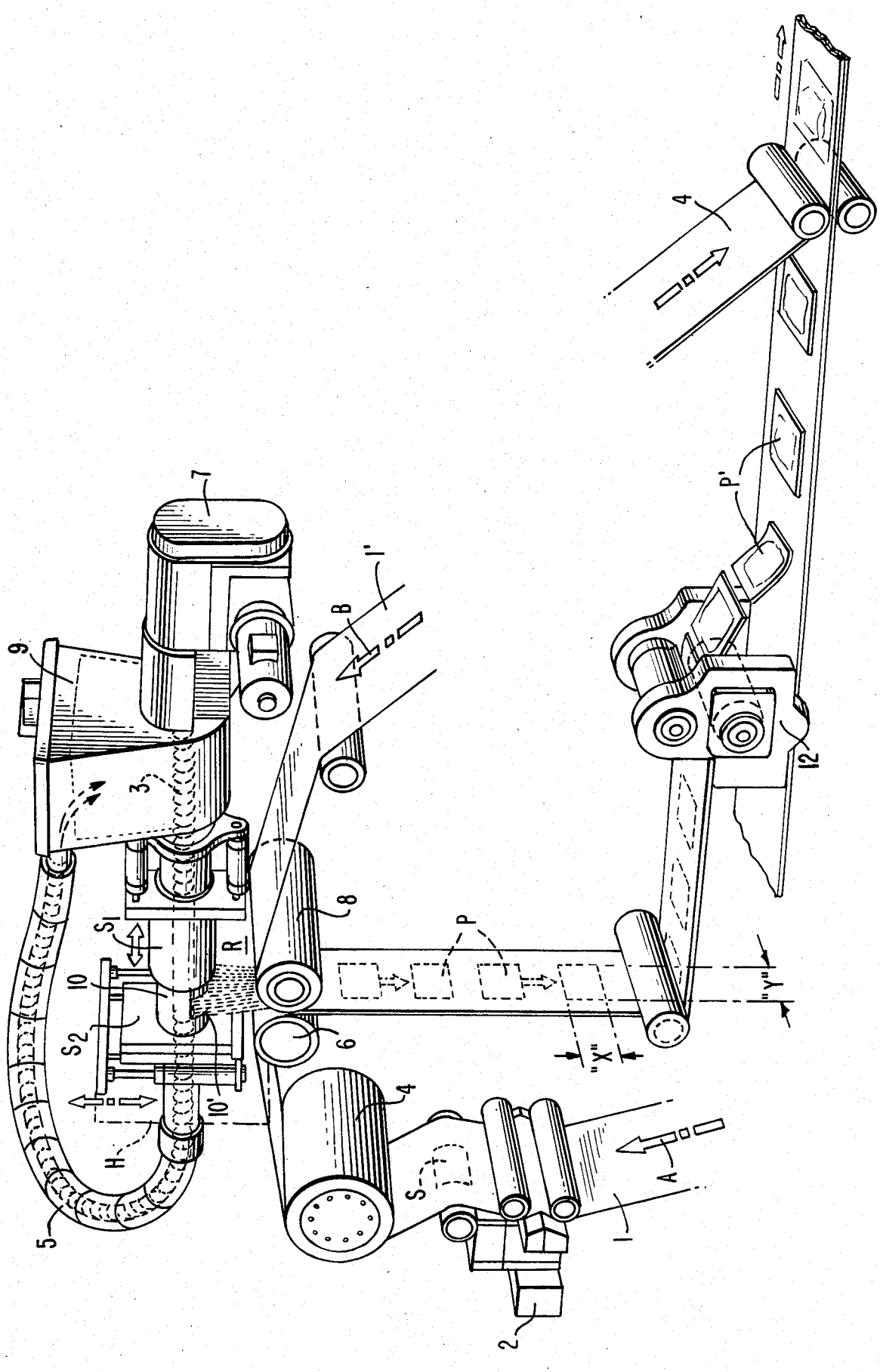

METHOD OF AND APPARATUS FOR MAKING POWDER-FILLED POUCHES AND THE LIKE

The present invention relates to methods of and apparatus for making powder-filled pouches and the like, being more particularly, though not exclusively, concerned with the packaging or adding of moisture-absorbent or other powder or powder-like materials to products that are to contain the same, but without exposing the fabricator or user to the risk of inhaling the powder—particularly very light powder materials that have a tendency to float or disperse into the atmosphere and can create a respiratory health hazard.

For purposes of illustration only, the invention will be described with reference to super-absorbent powders as of acrylated expanded steel/polymer materials and the like, that absorb a thousand or more times their own weight and are extremely light and highly useful for childrens or adult diapers and other applications. In accordance with the invention, techniques have been evolved for providing intermittent registered or metered quantities of powder in a continuous in-line or off-line pouch-fabricating and filling procedure, shielded or otherwise remote from the operator, and secure for the user.

An object of the present invention, accordingly, is to provide a new and improved method of and apparatus for making powder-filled pouches and that are particularly designed, through novel powder-extrusion head design, to minimize the escape of powder during pouch fabrication.

A further object is to provide a novel powder-filling pouch technique of more general utility as well.

Other and further objects will be explained hereinafter and are more particularly delineated in the appended claims.

In summary, from one of its important aspects, the invention embraces a method of providing sealed pouches of metered quantities of powdered material, that comprises, passing a first web past a hot melt adhesive applicating region, periodically applying spaced hot melt stripes defining the desired pouch perimeter to the web, carrying the first web to a region to which a second web is carried for lamination therewith, feeding powdered material from a source thereof along a predetermined path, intermittently gating the feeding to bring a metered quantity of powder to a location in said path directly over the said region where the webs are to be laminated, dropping the metered quantity of powder material from said location into said region synchronously with the presentation thereat of the hot melt adhesive stripes on the first web, and laminating the webs to close off the pouches at the successive hot melt stripe perimeter, with the metered quantity of powder sealed therewithin.

In machinery form, the invention contemplates apparatus for making sealed pouches containing powdered material, having, in combination, means for passing first and second webs to and over laminating rolls, means for periodically applying hot melt stripes defining the desired pouch perimeter to the first web so that lamination with the second web will close off the successive pouches, means for extruding powdered material along a predetermined path above the region of the laminating rolls, means for intermittently gating the powdered material extruding means at a location along said predetermined path directly over the said region of the laminating rolls to drop the gated metered quantities of powdered material from said location into said region between the webs as they are about to enter the laminating rolls, and means for synchronizing said powdered material extruding and gating means with the presentation at said region of the sucessive hot melt adhesive stripes on said first web, such that passing of the first and second webs through the laminating rolls closes-off the successive pouches with the metered quantity of powdered material sealed therewithin.

A preferred and best mode embodiment and details are hereinafter presented.

The invention will now be described with reference to the accompanying drawing, the single FIGURE of which is an isometric view of a preferred apparatus for practicing the method underlying the invention.

Referring to the drawing, a thin porous tissue or other "non-woven" web 1 (for the exemplary moisture-absorbent pouch illustration of the principles of the invention) is shown drawn in the direction of the arrow A past a hot melt application head 2 as, for example, of the slot nozzle metered intermittent type described in U.S. Pat. No. 3,595,204, where hot melt stripes are periodically or intermittently applied as from horizontal and vertical slot nozzles in the head 2 (shown dotted at S) to define the extended pouch perimeter. The web is carried over a chill roller 4 to cover the hot melt stripes so that they are ready for adhesive lamination, and is carried over and vertically downwardly at a lefthand steel laminating roller cooperating with a soft laminating roller 8, over which a thin porous tissue, "non-woven" or poly film or other plastic film web 1' is fed as shown at B. It is in the region R just above the laminating rollers 6 and 8 that powdered material is released in metered quantities from a powder-extrusion tube 10 and is dropped under the influence of gravity at the synchronous time that the hot-melt perimeter stripes S on the web 1 are being presented for lamination with the web 1' at the adjacent cooperating surfaces of the laminating rollers 6 and 8. This nipping lamination closes off the formed pouches P with the metered quantity of powder sealed therewithin. The region embracing the powder extrusion and releasing above the laminating rolls may be shielded by a housing schematically illustrated at H.

The vertical web of periodic super-absorbent powder-filled pouches, or at least partially porous pouches (as if one of the webs is polyfilm or the like), is horizontally (about 90° turn) carried to a rotary cut-off knife station 12, to produce separate successive pouches P' that may be laminated with an appropriate diaper web material 4. The multi-pouch web can be passed in-line with a diaper making/napkin making machine. In this case, the rotary knife system 12 would cut the powdered web into individual pouches for direct feeding into the diaper. In an off-line arrangement, the pouched web would wind up into a large roll. The roll would be installed into the diaper making machine and unwound and cut off into individual pouch segments, synchronously and in register to the diaper machine production. This latter process would be the same as though the pouch making system was placed in-line as described earlier.

Returning to the details of the extruder 10, this is illustrated in the form a helical screw extruder 3 extending from under the lower region of the powder material hopper 9, horizontally through the centrally located extrusion tube region and along a flexible screw return feeder path 5. The helical extruder 3 is end driven by a drive 7 and, above the powder-dispensing region R, is provided to the right at the beginning of the metering location with a first shutter S1 that intermittently cycles open; and, to the left at the end of such location, with a second shutter S2 that closes when the shutter S opens. The "x" length of the powder pocket is determined by the cycling rate of shutter gate S1, and the "Y" width, by the extruder tube diameter—the bottom opening 10' in the extruder tube thus dropping the shutter-controlled or metered quantity of extruded powder carried by the helical screw into that region.

The screw 8 is driven synchronous to web speed, so as always to deliver the same increments of powder weight irrespective of line speed. The two shutter valves S1 and S2 located at the end of the screw feed barrel system provide for application of the powder in an intermittently and registered pattern, the powder being applied at the location the two webs become laminated, as before explained. The two shutter valves provide a means of directing 100% of all powder supply to the return line/flexible screw region 5 to the reservoir hopper 9, or apply 100% of the screw feed supply to the laminating web. During powder application to the web, the shutter S1 is thus open, whereas shutter S2 is closed. In the "OFF" cycle, having no powder application, shutter S1 is closed, whereas shutter S2 is open for the return supply of powder to the hopper reservoir. The speed rate of powder return may be greater than the supply rate. Typical powder weights applied are 1–3 grams per pouch. Typical pouches can range in size from 2" wide×6" long, up to 6" wide×18" long, depending upon the type of napkin or diaper product to be made.

Further modifications will occur to those skilled in this art, and such are considered to fall within the spirit and scope of the invention as defined in the appended claims.

What is claimed is:

1. A method of providing sealed pouches of metered quantities of powdered material, that comprises, passing a first web past a hot melt adhesive applicating region, periodically applying spaced hot melt stripes defining the desired pouch perimeter to the web, carrying the first web to a region to which a second web is carried for lamination therewith, feeding powdered material from a source thereof along a predetermined path, intermittently gating the feeding to bring a metered quantity of powder to a location in said path directly over the said region where the webs are to be laminated, dropping the metered quantity of powder material from said location into said region synchronously with the presentation thereat of the hot melt adhesive stripes on the first web, and laminating the webs to close off the pouches at the successive hot melt stripe perimeter, with the metered quantity of powder sealed therewithin.

2. A method as claimed in claim 1 wherein the feeding of the powdered material along said path is effected by helical extruding, the timing of the gating of the extruding determining the metered quantity of powdered material at said location and with gravity enabling the falling of the powdered material between the webs as the hot melt stripe perimeter is being presented by said first web at said region.

3. A method as claimed in claim 1 where the helical extruding is effected by feeding the powdered material along a helical path, opening a first gate at an appropriate point prior to said location, helically extruding the powdered material through the first gate into said location above said region, and closing the first gate when the metered quantity has passed thereby into said location at which it falls toward the webs as they are about to be laminated.

4. A method as claimed in claim 3 and in which a second gate at the end of said location along said path is opened upon the closing of the first gate, and remaining powdered material is fed back to the source of powdered material.

5. A method as claimed in claim 1 and in which said powdered material is selected to be moisture-absorbent powder material and said first web is of thin porous material as used in diapers and surfaces to be kept relatively dry, the further web closing off the pouch being of at least one of thin porous material and thin plastic film.

6. A method as claimed in claim 5 and in which the successive powder-filled pouches are cut from the laminated webs and then successively applied to a diaper web.

7. Apparatus for making sealed pouches containing powdered material, having, in combination, means for passing first and second webs to and over laminating rolls, means for periodically applying hot melt stripes defining the desired pouch perimeter to the first web so that lamination with the second web will close off the successive pouches, means for extruding powdered material along a predetermined path above the region of the laminating rolls, means for intermittently gating the powdered material extruding means at a location along said predetermined path directly over the said region of the laminating rolls to drop the gated metered quantities of powdered material from said location into said region between the webs as they are about to enter the laminating rolls, and means for synchronizing said powdered material extruding and gating means with the presentation at said region of the successive hot melt adhesive stripes on said first web, such that passing of the first and second webs through the laminating rolls closes-off the successive pouches with the metered quantity of powdered material sealed therewithin.

8. Apparatus as claimed in claim 7 and in which means is provided for feeding said laminated first and second webs carrying the successive powdered material-filled pouches to cutter means for cutting off the successive pouches.

9. Apparatus as claimed in claim 8 and in which said powdered material comprises moisture-absorbing material as for use in diapers and the like, said first web is of diaper material as of tissue and non-woven sheet material, and said second web is of one of similar sheet material and thin plastic film.

10. Apparatus as claimed in claim 7 and in which said powdered material extrusion and gating means comprises a helical extruder fed from a source of powdered material with first and second gate shutters at the beginning and end of said location, respectively, and with the extruder open at its bottom over said location, said synchronizing means causing the first gate shutter to be open and the second shutter gate closed during the extrusion in said location and the dropping of the powdered material through said open bottom into said region for filling a pouch.

11. Apparatus as claimed in claim 10 and in which means is provided operable upon the closing of the first shutter gate to open the second shutter gate and carry excess extruded material back to said source.

12. Apparatus as claimed in claim 10 and in which the dimension of the dropping powdered material corresponding roughly to the pouch width is determined by the size of the bottom opening of the extruder over said location, and the quantity of powdered material corresponding roughly to the pouch length is determined by the rate of intermittent operation of the gating means.

13. Apparatus as claimed in claim 7 and in which said extruding means and said region between the same and the laminating rolls are housed in a shielding enclosure.

14. A method as claimed in claim 1 and in which the laminated filled-pouch-containing web is wound into a roll for subsequent off-line cutting and inserting use.

* * * * *